United States Patent [19]

DesRosier et al.

[11] Patent Number: 4,868,110

[45] Date of Patent: Sep. 19, 1989

[54] METHODS AND DEVICE FOR DETECTION OF MICROORGANISMS

[75] Inventors: John P. DesRosier; N. Robert Ward, Jr., both of Seattle, Wash.

[73] Assignee: BioControl Systems, Inc., Bothell, Wash.

[21] Appl. No.: 915,634

[22] Filed: Oct. 6, 1986

[51] Int. Cl.[4] .................... C12M 1/24; C12M 3/00; C12Q 1/04

[52] U.S. Cl. .................... 435/34; 422/102; 435/39; 435/40; 435/284; 435/297; 435/299; 435/301; 435/807

[58] Field of Search ............ 435/34, 39, 40, 284, 435/297, 299, 301, 807; 422/102

[56] References Cited

U.S. PATENT DOCUMENTS

| 3,603,156 | 9/1971 | Konkol | 422/102 X |
| 4,314,029 | 2/1982 | Ohtake et al. | 435/807 X |
| 4,579,631 | 4/1986 | Ishikawa et al. | 435/807 X |

OTHER PUBLICATIONS

Brock et al., *Biology of Microorganisms,* 4th ed. pp. 217, 218, 785, and 588–591, Prentice-Hall, Inc., Englewood Cliffs, N.J. (1984).
Oblinger et al., "The Most Probable Number Technique" chapter 6, in *Compendium of Methods for the Microbiological Analysis of Foods,* Speck ed., 2nd ed. pp. 99–111, Amer. Public Health Assoc., Washington, D.C. (1984).
Feng et al., "Fluorogenic Assays for Immediate Confirmation of *Escherichia coli,*" *Appl. Environ. Micro.,* 43, pp. 1320–1329 (1982).
Diaco, "The MUG Assay: New Approach to Food Testing" in *Agri. Biotech. News,* (1985).
Robison, "Evaluation of a Fluorogenic Assay for Detection of *Escherichia coli* in Foods", *Appl. Environ. Micro.,* 48, pp. 285–288 (1984).
Moberg, "Fluorogenic Assay for Rapid Detection of *Escherichia coli* in Food," *Appl. Environ. Micro.,* 50, pp. 1383–1387 (1985).

*Primary Examiner*—Barry S. Richman
*Assistant Examiner*—Jill Johnston
*Attorney, Agent, or Firm*—Seed and Berry

[57] ABSTRACT

A device is adapted for containing a volume of growth medium and employed for detection of gas produced by a microorganism or microorganisms putatively contained within a test sample and added to the growth medium, comprising a primary chamber, a dome defined by the top surface of the primary chamber and communicating therewith, the dome establishing a fluid level and adapted for collection of gas produced by a microorganism within the growth medium, and a fill section adjacent to and communicating with one end of the primary chamber, the fill section spaced apart from the dome and extending above the fluid level, and further defining an opening for the addition of a test sample. The device may be sealed by means of a removable closure. An apparatus also consists of an array of substantially identical devices is also disclosed. In addition, methods of using the device and apparatus for detecting and estimating numbers of microorganisms, and for analyzing samples putatively containing a microorganism, are described.

68 Claims, 1 Drawing Sheet

METHODS AND DEVICE FOR DETECTION OF MICROORGANISMS

DESCRIPTION

1. Technical Field

The present invention relates to an improved device for detection and estimation of numbers of microorganisms. The invention facilitates inoculation and incubation of cultures and collection and visualization of gas from the cultures. More particularly, this invention relates to a device, an apparatus, and methods for detecting gas produced from the metabolism of certain chemical substances by samples of pure or mixed cultures of microorganisms. The invention may also be used with fluorogenic and chromogenic substrates to detect the presence of specific microorganisms within a sample.

2. Background Art

Identification of a specific microorganism or a group of microorganisms within a natural sample can provide useful information. This information may be necessary for decision-making in cases of possible contamination or infection. The information may be used to make retrospective or predictive judgments about an identified sample. For instance, the detection of coliform bacteria within a food, dairy or water sample suggests fecal contamination of that sample, and in many instances, cautions against human consumption for fear of gastroenteritic disease. Alternatively, isolation of a characteristic bacterium from an individual with a specific clinical presentation usually establishes a diagnosis and course of therapy for that individual.

Samples which are suspected of harboring certain microorganisms are analyzed by prescribed methodologies designed to demonstrate the presence of a taxonomically defined category of microorganisms. The more common characteristics which are used to distinguish microorganisms are morphology and ultrastructure, staining reactions, physiological and biochemical activities, and ecology. The physiological and biochemical reactions that microorganisms perform are among the most useful characteristics for identification. Typically, a population of microorganisms is assayed for the ability to utilize a specific substrate for growth, or to convert that substrate to a characteristic product. Growth is usually indicated by formation of a visible mass of cells on a solid growth medium or by the development of turbidity in liquid growth medium. Formation of a characteristic product may be accompanied by a change in color (from a change in pH or oxidation-reduction potential or from enzymatic cleavage of a chromogenic compound), development of fluorescence, deposition of a precipitate, or accumulation of gas in the growth medium.

In the fields of water, dairy, and food microbiology, samples are regularly monitored for the presence of microbial contaminants. Food, dairy, and water samples are tested for critical concentrations of organisms chosen as indicators of the presence of pathogens. Testing for indicators avoids the necessity of assaying for every conceivable pathogenic microorganism. The group of aerobic and facultatively anaerobic, Gram-negative, non-spore-forming, rod-shaped bacteria that ferments lactose with gas production within 48 hours when incubated at 35° C, is designated the coliform bacteria, and is widely used as an indicator. Some coliform bacteria, such as *Escherichia coli*, are associated with fecal contamination.

The taxonomic breadth of microbial identification may be altered for specific applications For example, the epidemiologist may desire categorization at the level of subspecies or variant, while the sanitarian may limit identification to an operationally defined group, such as the coliform bacteria. At either extreme of taxonomic determination, millions of identifications are performed annually, with many of the assays involving tedious steps and requiring considerable laboratory space and equipment. Consequently, a method which provides easy and efficient microbial detection, identification, or estimation will save the laboratory considerable time and money.

One technique frequently used for the estimation of coliform bacteria in food and water samples is the most-probable number (MPN) test. The MPN test is based on probability statistics, and results are directly related to the frequency of occurrence of a series of positive results when given numbers of microorganisms are present in a sample. The MPN technique is based on two assumptions. First, if a sample contains microorganisms, the microorganisms are randomly distributed throughout a dilution or homogenate of the sample. Second, when an aliquot of culture medium is inoculated with a viable cell and processed properly, a "positive" result will be observed.

Both the MPN procedure and the direct plating technique are used to quantitate viable microorganisms. However, for many samples, plating of diluted samples on agar plates and direct counting of resultant colonies are not feasible. Certain bacteria will not grow on any solid medium, and thus require cultivation in liquid medium. The nature of some food products makes standard plating procedures difficult, because of particulates and low microbial density (i.e., <10 organisms/gm). The MPN procedure utilizes liquid growth media, and permits greater flexibility in inoculum volume and greater sensitivity at low microbial density. The use of liquid media often enhances the recovery of microorganisms that have been debilitated by processes such as heating, drying, or the addition of a disinfectant or sanitizing agent.

Specifically, the MPN technique requires dilution of a test sample until the microbial density is less than one viable cell per milliliter. Replicate aliquots are removed from appropriately diluted samples, inoculated into separate tubes of growth medium, and incubated to allow growth. Usually three to five serial 10-fold dilutions are tested. Tubes inoculated with one or more viable cells will demonstrate growth; those that did not receive a viable cell will not demonstrate growth. The proportion of tubes that demonstrate growth is a measure of the probability of receiving a viable cell. This probability can be converted back into cell concentration by use of statistical tables, constructed for use with three, five, or ten replicate samples per dilution. Accuracy of the MPN test increases as the number of replicates per dilution increases.

The MPN procedure may be used to estimate the total number of viable organisms, as well as the number of a variety of specific bacteria or groups of bacteria. Each MPN estimation is accomplished through detection of characteristics that are unique to that organism or group of organisms. For example, gas production resulting from the fermentation of lactose under appropriate conditions is used to estimate coliform concentrations through use of the MPN procedure (designated the coliform MPN procedure).

Within this application, any microorganism that produces gas during metabolism will be referred to as an "aerogenic microorganism." In a modification of the coliform MPN procedure, fluorogenic or chromogenic substrates may be added to the growth medium. For instance, non-fluorescent or non-colored agents may be cleaved specifically by the coliform bacterium *E. coli* to yield a fluorescent or colored product. Inoculated growth medium containing a fluorogenic or chromogenic substrate would be examined after 24 h at 35° C under an appropriate light source, and the presence of fluorescence or color would indicate the presence of *E. coli* in the test sample. Such medium modification thus permits the additional identification of coliform samples that specifically contain *E. coli*. In addition, the MPN format in which the test was conducted may permit a separate estimation of the number of *E. coli* in the sample.

At present, several devices or methods are available for performing coliform MPN tests, but all possess certain disadvantages. Most MPN methods that allow detection of gas production by growing bacteria rely on the displacement of culture fluid by the gas produced to form a visually detectable bubble. One such gas detection method employs a J- or V-shaped culture vessel or fermentation tube containing one open and one closed end. Liquid growth medium is placed into the open end of the tube, and the tube is tilted so that the medium fills the closed arm of the V. The tube is then inoculated and incubated, and any gas produced within the closed arm of the V rises and accumulates at the top of the V arm. This method is useful for both qualitative and quantitative gas determinations, but suffers from several drawbacks. First, the J- or V- tubes employed are blown glass and are relatively expensive. Furthermore, the tubes are delicate because they sit on a pedestal, and the multiple operations that are required for their use (e.g., washing, sterilizing, filling, inoculating, and handling to and from the incubator) make them both susceptible to breakage and inconvenient to use. Moreover, this susceptibility to breakage and spillage poses a special biohazard when pathogenic microorganisms have been cultured. Finally, the tubes are bulky and require a large amount of incubator space, making the simultaneous performance of multiple tests unfeasible. As a result of the limitations noted above, V- and J-tubes have not received general acceptance for use with the MPN procedure.

The most widely used and presently preferred method for gas entrapment and detection in conjunction with MPN determinations employs a capped test tube containing liquid growth medium. Disposed within this capped tube is a second, smaller diameter Durham tube that is inverted in the growth medium. When the test tube is inoculated with aerogenic bacteria and incubated, gas produced by microorganisms collects and forms a bubble under the inverted Durham tube.

For MPN determination using test tubes containing Durham tubes, inoculated tubes are often placed in a three-by-three array in a test tube rack (i.e., three replicates of three 10-fold dilutions). After incubation, the tubes are observed for gas production. The Durham tube method is suboptimal, because only the gas produced by microorganisms under the Durham tube is collected, and consequently, only a fraction of the culture's aerogenic potential is sampled. Second, air must be evacuated from the Durham tube by heat sterilization. This step suffers from the disadvantage that some growth components are heat labile (e.g., sugars), and therefore must be added separately to each culture tube from a filter-sterilized stock after the heating step. Third, air may be inadvertantly introduced into the Durham tube upon addition of the inoculum.

Another method for MPN estimation through detection of trapped gas involves overlaying an inoculated test tube of broth medium with heavy mineral oil or molten agar. These overlayed substrates form a barrier at the top of the broth medium under which gas bubbles collect. This overlay method has several drawbacks: (1) it is tedious, since it requires a separate addition to each culture tube; (2) it requires a high degree of skill to overlay molten agar on a liquid medium; (3) it is time-consuming, because it involves separate preparation of the overlay materials and sterile addition to culture tubes; and (4) in the case of a mineral oil overlay, the method is unreliable because bubbles frequently escape between the test tube wall/mineral oil interface.

A more recent method utilizing gas entrapment and visualization is exemplified by the 3M product, Petrifilm. When Petrifilm is inoculated with a liquid sample a gel-containing growth medium is rehydrated. The inoculated medium is sandwiched between two plastic film sheets, forming a thin layer for incubation. Bacterial colonies are detected as stained masses of cells, due to the incorporation of a dye in the growth medium. Gas produced by microorganisms within a colony is entrapped between the layers of the film immediately adjacent to the colony. This sandwich method, however, requires a degree of skill for inoculation and "sandwiching" of the inoculum between the two layers of film. The Petrifilm method may be used for viable coliform quantitation, but is not practical to use in an MPN format.

In addition to the noted disadvantages of current gas detection methods, as employed with a small number of samples, all of the described methods become even more inconvenient when used for large-scale testing of multiple samples. Monitoring of gas production by any of the methods noted above dictates that separate units of the particular gas collection apparatus be individually handled during preparation, inoculation, incubation, and visualization of the results for each sample tested. These multiple independent operations present problems in handling, spatial inefficiency in storage and incubation, and inconvenience during visualization of gas production.

There is a need in the art, therefore, for a gas collection device or apparatus that entraps gas efficiently and provides single or multiple tests in a stable, easy-to-handle, spatially efficient manner. The present invention fulfills this need and further provides other related advantages.

DISCLOSURE OF THE INVENTION

One aspect of the present invention relates to a device adapted for containing a volume of growth medium, the device employed for detection of gas produced by a microorganism or microorganisms putatively contained within a sample added to the growth medium, comprising a primary chamber having a top surface, a dome defined by the top surface of the primary chamber and communicating therewith, the dome establishes a fluid level and is adapted for collection of the gas produced by a microorganism or microorganisms within the growth medium, and a fill section adjacent to and communicating with one end of the primary chamber, the fill section spaced apart from the dome and extending above the fluid level, and further defining an opening for the addition of the test inoculum.

A second aspect of the present invention relates to an apparatus consisting of an array of adjacent, substantially identical devices, each device adapted for containing a volume of growth medium and employed for detection of gas produced by a microorganism putatively contained within a test sample added to the growth medium of each device, each device comprising a primary chamber having a top surface, a dome defined by the top surface of the primary chamber and communicating therewith, the dome establishes a fluid level and is adapted for collection of the gas produced by the microorganism or microorganisms within the growth medium, a fill section adjacent to and communicating with one end of the primary chamber, the fill section spaced apart from the dome and extending above the fluid level, and further defining an opening for the addition of the test sample, and means for selectively closing the opening defined by the fill section. Apparati consisting of three-by-three and three-by-five arrays of the device are preferred.

A method for detecting the presence of aerogenic microorganisms within a sample putatively containing a microorganism utilizing the device of the present invention, comprising the steps of adding growth medium to the device, adding the sample to the growth medium, thereby forming a mixture, incubating the mixture, and detecting the presence of aerogenic microorganisms by determining the presence or absence of gas within the device is disclosed. Preferred samples include water, dairy and food samples, and biological fluids.

A method for detecting the presence of aerogenic microorganisms in a plurality of samples putatively containing a microorganism utilizing the apparatus of the present invention, comprising the steps of adding growth medium to at least two devices of the apparatus, adding the samples to the devices containing the growth medium, thereby forming mixtures, incubating the mixtures, and detecting the presence of aerogenic microorganisms by determining the presence or absence of gas within each device is also disclosed.

Another embodiment of the invention discloses a method for estimating the number of aerogenic microorganisms within a sample utilizing the apparatus of the present invention, comprising the steps of adding growth medium to at least two devices of the apparatus, adding serial dilutions of a sample containing at least one aerogenic microorganism to the devices containing the growth medium, thereby forming mixtures, incubating the mixtures, and estimating the number of microorganisms within the sample.

A further aspect of the invention discloses a method of analyzing a sample putatively containing a microorganism utilizing the device of the present invention, comprising the steps of adding growth medium containing a fluorogenic or chromogenic substrate to the device, adding the sample to the growth medium, thereby forming a mixture, incubating the mixture, detecting the presence of aerogenic microorganisms by determining the presence or absence of gas within the device, and determining the presence of microorganisms by detecting the presence or absence of fluorescent or colored products within the growth medium.

Yet another aspect of the invention describes a method for analyzing a plurality of samples, each putatively containing a microorganism or microorganisms utilizing the apparatus of the present invention, comprising the steps of adding growth medium containing a fluorogenic or chromogenic substrate to at least two devices of the apparatus, adding the samples to the devices containing the growth medium, thereby forming mixtures, incubating the mixtures, detecting the presence of microorganisms by determining the presence or absence of gas within each device, and determining the presence of microorganisms by detecting the presence or absence of fluorescent or colored products within the growth medium.

A method of analyzing microorganisms within a sample utilizing the apparatus of the present invention, comprising the steps of adding growth medium containing a fluorogenic or chromogenic substrate to at least two devices of the apparatus, adding serial dilutions of a sample containing at least one microorganism to the devices containing the growth medium, thereby forming mixtures, incubating the mixtures, estimating the number of aerogenic microorganisms within the sample, and determining the presence of microorganisms by detecting the presence or absence of fluorescent or colored products within the growth medium.

BEST MODE FOR CARRYING OUT THE INVENTION

As noted above, current devices and techniques for detecting gas production are accompanied by numerous disadvantages. Presently available methods are tedious, time-consuming, and/or require a certain level of skill to perform reproducibly. In addition, some methods of gas detection do not maximize gas collection, since only a portion of the gas produced by a given microbial culture is collected for detection. Various devices employed for gas collection and detection are fragile, cumbersome, and/or spatially inconvenient. Further, the devices presently used for gas collection and detection are susceptible to spillage of biohazardous materials contained within the devices. In addition, because tests utilizing gas collection, such as the MPN technique, are often done on a large scale, the disadvantages noted above become amplified.

The present invention describes a simple, improved device for entrapment and visualization of gas produced by microorganisms within a liquid growth medium. The present device provides a more efficient means of gas collection and is well suited to the multiple unit testing needed for estimation by the MPN procedure of the number of microorganisms present in numerous test samples.

Figures 1, 2, 3:
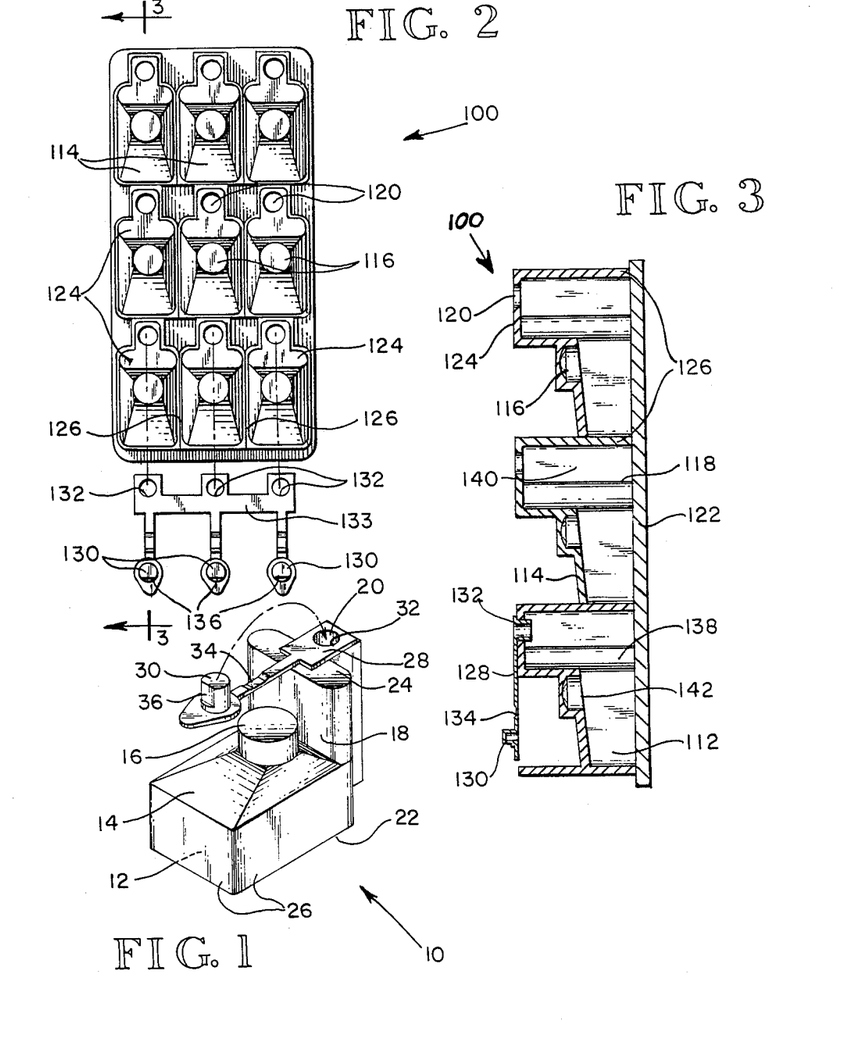
FIG. 1 is an isometric view of a preferred embodiment of an apparatus constructed according to the principles of the present invention.
FIG. 2 is a top plan view of an alternative preferred embodiment of the present invention, comprising a two-dimensional array of devices as depicted in FIG. 1.
FIG. 3 represents a cross section of the apparatus shown in FIG. 2, on the line designated 3—3.

Referring to FIG. 1, a preferred embodiment of the gas collection device 10 of the present invention is shown. The gas collection device 10 may be constructed from transparent materials, such as plastic or glass. This device comprises a primary chamber 12 for accommodating a volume of growth medium. The base 22 of the primary chamber 12 is substantially rectangular, with opposite walls 26 being substantially mutually parallel, and adjacent walls 26 being substantially mutually perpendicular. The primary chamber 12 has a top surface 14 that defines a dome 16. The dome 16 is adapted to collect gas produced by microorganisms contained within the primary chamber 12. The dome 16 extends above the top surface 14, and the highest interior point of the dome 14 establishes a fluid level. The top surface 14 is slanted upwardly toward the dome 16 to facilitate entrapment of gas within the dome 16.

A fill section 18 is positioned adjacent to one end of the primary chamber 12, and communicates with the primary chamber 12. The fill section 18 extends above the fluid level established by the dome 16. In addition, the fill section 18 is spaced apart from the dome 16 of the top surface 14. The fill section 18 and the primary chamber 12 share a contiguous base 22 that is substantially perpendicular to the walls 26 of the primary chamber 12. An inlet surface 24 defines the upper boundary of the fill section 18, and further defines an opening 20 for the introduction of a test sample (not shown) into the primary chamber 12. In a preferred embodiment, the inlet surface 24 is substantially parallel to the base 22.

The openings 20 of the device 10 may be selectively closed by means of a removable closure 28. The removable closure comprises a plug 30 that is coupled to a plastic insert 32 by means of a flexible hinge 34. The outer surface of the plastic insert 32 frictionally engages the inner surface of the opening 20 to provide a first seal therebetween. When the associated plug 30 is fully depressed into the opening 20, a second seal is created between the outer periphery of the plug 30 and the inner surface of the plastic insert 32. In a preferred embodiment, the first and second seals created are hermetic seals. The outer surface of the plug 30 defines a flat surface 36 that provides for selective venting of the device 10 through partial insertion of the plug 30 into the plastic insert 32. Partial insertion of the plug 30 creates a gap between the flat surface 36 and the inner surface of the plastic insert 32 to allow pressure equalization between the interior of the device 10 and the atmosphere.

In an alternative preferred embodiment, shown in FIGS. 2 and 3, an apparatus 100 comprises an array of substantially identical, adjacent units of a gas collection device 10. In a preferred embodiment, the apparatus 100 contains three rows and three columns of adjacent units of the gas collection device 10, with the fill sections 118 disposed proximal to one end of the apparatus 100. It would be obvious to one skilled in the art that arrays comprising other combinations of rows and columns of adjacent units could be employed. For example, a three-by-three, a three-by-five, a five-by-five or a one-by-five array may be preferred for some applications.

All devices within the apparatus 100 preferably share a contiguous base 122, and all adjacent primary chambers 112 share at least one contiguous wall 126. Within the apparatus 100, opposite walls 126 of the primary chambers 112 are substantially mutually parallel, and adjacent walls 126 are substantially mutually perpendicular.

Each primary chamber 112 has a top surface 114 that defines a dome 116. The dome 116 extends above the top surface 114, and the highest interior point of the dome 16 establishes a fluid level. Gas produced by microorganisms contained within the primary chamber 112 collects in the dome 116. The top surface 114 is slanted upwardly to facilitate the entrapment of gas within the dome 116.

Each device of the apparatus 100 has a fill section 118 that is disposed adjacent to and communicates with one end of a primary chamber 112. Along one axis of an apparatus 100, fill sections 118 would be disposed adjacent to each other. Along the perpendicular axis of an apparatus 100, fill sections 118 would be disposed adjacent to, but would not communicate with, a primary chamber 112.

Each fill section 118 extends above the fluid level established by a dome 116, and is spaced apart from dome 116. Each fill section 118 is continuous with an inlet surface 124 that is substantially parallel to the base 122. Each inlet surface 124 further defines an opening 120 for the introduction of test samples (not shown) into the primary chamber 112.

FIG. 3 depicts the internal geometry of the apparatus 100 of FIG. 2, which comprises an array of devices, each of which has structure analogous to the device 10 shown in FIG. 1.

The fill section 18 defines an intermediate volume 138 and a distal volume 140. The intermediate volume 138 is selected to accommodate a volume of fluid, such that no part of the total volume of fluid added to the apparatus 100 can spill through the opening 120 as the apparatus 100 is tilted 70°–120° from a horizontal reference plane to purge gas from the dome 116. The distal volume 140 is designed to minimize the volume of fluid contained within the fill section 118 when the device is horizontally disposed.

The interior edge 142 of the dome 116 defines a plane which intersects the plane of the base 122, such that the portion of the edge 142 adjacent to the fill section 118 is elevated at a greater distance from the base 122 than that portion of the edge 142 that is distal to the fill section 118. This arrangement provides that a predetermined maximum volume of gas produced by microorganisms within the culture medium can be trapped within the dome 116, and that any additional volume of gas will be conveniently released into the fill section 118. Due to the analogous internal structure of the preferred embodiment device 10 of FIG. 1 and each device of the preferred embodiment apparatus 100 of FIG. 3, there exists comparable functionality between these embodiments.

The openings 120 of the apparatus 100 may be selectively closed by means of a removable closure 128. The removable closure 128 comprises three plugs 130, each coupled to a plastic insert 132 by means of a flexible hinge 134. The outer surface of the plastic insert 132 frictionally engages the inner surface of an opening 120 to provide a first seal therebetween. When fully depressed into the opening 120, a second seal is created between the outer periphery of the plug 130 and the inner surface of the plastic insert 132. In a preferred embodiment, the first and second seals created are hermetic seals. The outer surface of each plug 130 defines a flat surface 136 that provides for selective venting of a device by partially inserting the plug 130 into the plastic insert 132 that is frictionally engaged within the opening 120, thus creating a gap to allow pressure equalization between the interior of the device and the atmosphere.

The device and apparatus described above offer several advantages over gas collection devices previously available. Individual gas collection devices can be easily adapted into various arrays of chambers, facilitating multiple testing of numerous samples. While multiple testing with vertical tubes may lead to tipping and potential spilling of biohazardous materials, the major plane of the apparatus of the present invention is horizontal, offering stability and safety. Further, the gas collection devices, either singly or in an array, are self-supporting, and do not require the use of accessory racks, as with vertical tubes. The elimination of the need for racks makes the device, either singly or in an array, spatially more efficient. Further, the apparatus can be stacked vertically for storage, incubation, and sterilization after use, leading to spatial efficiency.

Another advantage of the apparatus is simultaneous air evacuation from the gas collection area. Currently available gas collection devices in which air was present or introduced into the gas collection compartment during preparation or inoculation would generally be discarded (Durham tubes) or evacuated individually (J-tubes). Apparati of the present invention facilitate simultaneous air evacuation through the simple process of tilting the apparatus.

The removable closure of the device may utilize an individual hinged plug, providing ease of opening and closing the entry to the device. The hinge ensures that plugs of the removable closures are not dropped, contaminated, or misplaced after removal from the plastic inserts. The two-position insertion of the plug allows the device to be either hermetically sealed or ventable. Coupling of removable closures in groups of three facilitates rapid removal and insertion of plugs into the apparatus.

A further advantage of the device or apparatus of the present invention is disposability. Durham tube and J-tube devices are sterilized after use, cleaned, and reused. These steps are cumbersome, time-consuming, and are accompanied by breakage The device and apparatus described above provide ease in handling, because the device or apparatus is merely disposed of after use. The device and apparatus are made of inexpensive, transparent materials, and are suited to large-scale production.

The device of the present invention further provides superior gas collection. The dome of the chamber collects gas from approximately 75% of the volume of the culture medium contained within the device. Improved collection of gas imparts more sensitivity to gas detection through use of the present invention as compared to the conventional Durham- or J-tube devices. In addition, if concentrated culture medium is utilized, the equilibration of the medium after inoculation of the sample is rapidly achieved through use of the present device. In contrast, use of concentrated medium with conventional devices is problematic, because the concentrated medium equilibrates slowly by diffusion after inoculation.

The device and apparatus described above are useful for the collection and detection of gas produced by microorganisms in test samples In an alternate preferred embodiment, the device may contain a sterile culture medium in a concentrated form. This culture medium is appropriately prepared so that the addition of an inoculum to the culture medium would result in a desired final concentration of culture medium. For instance, MPN testing of samples to determine the number of coliform bacteria contained within each of the samples would involve the addition of an inoculum to sterile growth medium in the device to yield a volume greater than the volume defined by the primary chamber, the top surface, and the dome of the device. The culture medium is placed in the device by means of the opening in the fill section of the device. After addition of an inoculum to the device, any air remaining in the dome of the top surface is easily and rapidly evacuated by tilting the device such that the dome is completely filled with growth medium. When the device is returned to the untilted position, the entire enclosure, as defined by the primary chamber, the top surface and the dome, is free of entrapped air. If air is subsequently introduced into the dome during further manipulations the device may be tilted at any time to once again remove entrapped air.

The device and apparatus provide a single-chamber format for performing presumptive and confirmatory stages of coliform MPN tests. For instance, cultures that produce gas after 24 or 48 hours may be confirmed as positive by supplementing the culture with a concentrated solution of brilliant green bile (BGB) medium to an appropriate final concentration. The device or apparatus is tilted several times to remove entrapped air and equilibrate the BGB medium. A successful single-chamber format, as described above, requires proper equilibration of supplemented medium, which cannot be rapidly achieved with J-tube or Durham tube devices, which depend on diffusion as noted above.

The presence of aerogenic microorganisms in a plurality of samples may be detected through inoculation of individual devices of the apparatus of the present invention. Further, the apparatus may be used for estimation of numbers of microorganisms within test samples, for example, by appropriately diluting test samples for MPN testing. Either three-by-three, three-by-five, five-by-five, or one-by-five arrays may be employed in a preferred embodiment, the choice of apparatus employed to be determined by the number of dilutions and the number of replicates to be tested. For MPN testing, triplicate samples from 10-fold dilutions may be added to each row of three devices through the opening in each fill section. Inoculated apparati may then be stacked for spatially efficient incubation.

In addition, the device and the apparatus of the present invention may be employed for the detection of microbial gas production and the detection of microbially produced fluorescence or color resulting from the hydrolysis of fluorogenic or chromogenic substrates in the growth medium. For instance, microbial enzyme reactions may provide a highly specific, rapid and sensitive assay for detection of specific strains of microorganisms.

Examples of suitable fluorogenic substrates which may be utilized within the present invention are listed in Table 1.

TABLE 1

Fluorogenic substrates
Fluorescein diacetate
4-Methylumbelliferyl acetate
4-Methylumbelliferyl casein
4-Methylumbelliferyl-α-L-arabinopyranoside
4-Methylumbelliferyl-β-D-fucopyranoside
4-Methylumbelliferyl-α-L-fucopyranoside
4-Methylumbelliferyl-β-L-fucopyranoside
4-Methylumbelliferyl-α-D-galactopyranoside
4-Methylumbelliferyl-β-D-galactopyranoside
4-Methylumbelliferyl-α-D-glucopyranoside 4-Methylumbelliferyl-β-D-glucopyranoside
4-Methylumbelliferyl-β-D-glucuronide
4-Methylumbelliferyl nonanoate
4-Methylumbelliferyl oleate
4-Methylumbelliferyl phosphate
bis(4-Methylumbelliferyl)phosphate
4-Methylumbelliferyl pyrophosphate diester
4-Methylumbelliferyl-β-D-xylopyranoside A list of suitable chromogenic substrates for use within the present invention is contained in Table 2.

TABLE 2

Chromogenic substrates
o-Nitrophenyl-β-D-galactopyranoside
p-Nitrophenyl-β-D-galactopyranoside
o-Nitrophenyl-β-D-glucopyranoside
p-Nitrophenyl-α-D-glucopyranoside
p-Nitrophenyl-β-D-glucopyranoside
p-Nitrophenyl-β-D-glucuronide
p-Nitrophenyl phosphate
o-Nitrophenyl-β-D-xylopyranoside
p-Nitrophenyl-α-D-xylopyranoside
p-Nitrophenyl-β-D-xylopyranoside
Phenolphthalein-β-D-glucuronide More specifically, approximately 97% of *E. coli* strains tested produce the enzyme β-glucuronidase, while other genera of Enterobacteriaceae generally do not synthesize this enzyme. Originally, β-glucuronidase was detected through use of chromogenic substrates, but recently a more sensitive assay for β-glucuronidase has been developed, utilizing the fluorogenic substrate 4-methylumbelliferyl-β-D-glucuronide (MUG). β-glucuronidase cleaves the non-fluorescent compound MUG, producing 4-methylumbelliferone, a highly fluorescent compound detected under long wave ultraviolet light. One advantage of MUG testing for *E. coli* is that anaerogenic strains of *E. coli* may be detected. Further, MUG detection of *E. coli* may be used in combination with the presumptive coliform MPN test to establish the presence and/or estimate the number of *E. coli* in a test sample. The use of MUG in MPN coliform media thus offers a rapid test for *E. coli* that can be performed with samples containing mixed populations of microorganisms.

A significant advantage of the present device is amenability to incorporation of colorimetric or fluorescent detection of specific strains of microorganisms into methods for improved gas visualization. For example, the fluorogenic substate MUG can be added to the MPN coliform medium to specifically detect the presence of *E. coli* in a test sample. The apparatus permits simultaneous detection of gas and colored or fluorescent products resulting from hydrolysis of chromogenic or fluorogenic substrates without further manipulation. In contrast, individual tubes utilized for MPN testing usually must be held in a vertical position for observation of color or fluorescence. Observation of fluorescence is difficult because the tubes must be positioned essentially perpendicular to the ultraviolet light source. Further, the apparatus of the present invention is designed to be adaptable to automated surface scanning fluorometers and colorimeters. The combination of the advantageous design features of the present invention with improved detection of colored or fluorescent enzymic products offers an improved, rapid, and easy method for detection and estimation of a specific group and a specific genus within a heterogeneous population of microorganisms.

To summarize the examples which follow, Example I describes a method for detection of gas produced by a microbial isolate tentatively identified as one capable of gas production. Example II relates to the detection of coliform bacteria in a water sample by the presence-absence technique, using the device of the present invention. Example III describes a method for estimation of numbers of coliform bacteria in food or water samples with the MPN technique, utilizing the apparatus of the present invention. Example IV relates to the estimation of numbers of coliform bacteria, as well as to the specific detection and estimation of *E. coli* in food samples, through use of the apparatus of the present invention in conjunction with a specific metabolic assay.

The following examples are offered by way of illustration and not by way of limitation.

EXAMPLE I

Detection of Microbial Gas Production by an Isolated Strain

A bacterial isolate tentatively identified by cultural characteristics as capable of gas production (e.g., *E. coli*) is inoculated into appropriate growth medium contained within the device. Briefly, 11 ml of purple broth (DIFCO) containing 0.5% lactose is sterilely pipetted into the gas collection device. The device is tilted to remove residual bubbles from the gas collection dome. A single colony tentatively identified as *E. coli* (possessing a green metallic sheen on Eosin methylene blue agar) is picked and suspended in phosphate buffered saline (PBS; pH 7.2). A loopful of the suspension is then transferred to the purple broth within the device, and the culture incubated at 37° C for 24 hours. Bacterial isolates capable of metabolizing lactose, with production of acid and gas end products, will demonstrate a color change from purple to yellow in the growth medium that is indicative of acid production. In addition the gaseous end products, hydrogen and carbon dioxide, will collect under the dome of the apparatus, permitting ready visualization.

EXAMPLE II

Detection of Coliform Bacteria in a Drinking Water Sample by the Presence-Absence Technique The device of the present invention may be used to assay water samples for the presence of coliform bacteria, according to the presence-absence technique described in *Standard Methods for the Examination of Water & Wastewater* (17th ed., American Public Health Association, 1981). Briefly, 100 ml of drinking water are aseptically added to 50 ml of triple strength Clark's medium in the device. The device is tilted to remove residual bubbles from the gas collection dome, subsequently incubated at 35° C, and inspected for the presence of gas and acid at 24 and 48 hours.

Presumptively positive cultures are then subcultured to confirm the presence of coliforms. A loopful of cell suspension is transferred from each gas-positive culture to an evacuated device containing 11 ml of brilliant green lactose bile medium. The subcultures are incubated at 35° C and examined at 24 and 48 hours for the presence of gas.

EXAMPLE III

Estimation of Numbers of Coliform Bacteria in Food and Water Samples by the MPN Technique Food or water samples may be assayed for coliform levels in the apparatus, according to methods described in *Compendium of Methods for the Microbiological Examination of Foods* (2nd ed., American Public Health Association, 1984) and *Standard Methods for the Examination of Water and Wastewater* (17th ed., American Public Health Association, 1981). For MPN testing of water samples, 1.0 ml aliquots of 10×concentrated lauryl tryptose broth were added to devices of an apparatus. Replicate 10 ml test samples were then aseptically added to each of five devices. The apparatus was tilted to remove residual gas bubbles from the gas collection dome and incubated at 35° C. At 24 and 48 hours, the domes of the devices were examined for the presence of gas.

Presumptively positive cultures were then subcultured to confirm the presence of coliforms. Briefly, a loopful of cell suspension was transferred from each gas-positive culture to an evacuated device containing 11 ml of brilliant green lactose bile medium. The inoculated subcultures were incubated at 35° C and examined at 24 and 48 hours for the presence of gas.

Food samples were diluted 10-fold prior to MPN assay. One part (by mass) of solid food was added to 9 parts (by volume) of sterile diluent buffer (Butterfield's Phosphate), and the mixture was blended for 2 minutes. Two additional serial 10-fold dilutions were made from the 1:10 diluted food sample. Ten ml of each 10-fold dilution were added to each of three separate devices of an apparatus, each containing 1.0 ml of 10×concentrated lauryl tryptose broth. The apparatus was then tilted to evacuate gas from the collection dome. The cultures were incubated at 35° C, and examined for the production of gas at 24 and 48 hours. A loopful of cell suspension was then transferred from each gas-positive culture to an evacuated device containing 11 ml of brilliant green lactose bile medium to confirm the presence of coliforms. The inoculated subcultures were incubated at 35° C and examined at 24 and 48 hours for the presence of gas. The number of devices that contain gas at each dilution is used to estimate the number of bacteria contained within the original sample through use of a standard statistical (MPN) probability table.

EXAMPLE IV

Detection of *E. coli* and Estimation of Numbers of Coliforms and *E. coli* in Food Samples by the MPN Technique The presence of *E. coli* in food samples may be specifically detected and estimated in an MPN assay by adding 4-methylumbelliferyl-$\beta$-D-glucuronide (MUG) to lauryl tryptose broth. Briefly, food samples were diluted 10-fold (1 part mass of solid food to 9 parts volume sterile diluent buffer), and the mixture blended for 2 minutes. Two additional serial 10-fold dilutions were made. Ten ml aliquots from each 10-fold dilution were added to each of 3 separate devices of an apparatus, each containing 1.0 ml of 10×concentrated lauryl tryptose broth, supplemented with 50 ug/ml MUG. The apparatus was tilted to remove residual bubbles from the gas collection dome. The cultures were incubated at 35° C, and inspected for gas production at 24 and 48 hours. In addition, the apparati were examined at 24 hours under long-wave ultraviolet illumination for fluorescence resulting from $\beta$-glucuronidase cleavage of MUG. Inoculated cultures were compared to an uninoculated device to determine positive fluorescence. Devices exhibiting fluorescence with or without gas are considered to be positive for the presence of *E. coli*. Gas and fluorescence at the various dilutions are used to estimate the number of coliforms (gas) and *E. coli* (fluorescence) through use of a standard statistical (MPN) probability table.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A device adapted for containing a volume of a growth medium, said device employed for detection of gas produced by a microorganism putatively contained within a test sample added to the growth medium, comprising:

a primary chamber having a top surface and a base;

a dome defined by said top surface of said primary chamber and communicating therewith, said dome establishing a fluid level defined by the highest interior part of the dome, and being adapted for collection of gas produced within said growth medium; and a fill section adjacent to and communicating with one end of said primary chamber, said fill section spaced apart from said dome and extending above said fluid level, and further defining an opening for the addition of said test sample.

2. The device of claim 1, additionally comprising a means for selectively closing said opening defined by said fill section.

3. The device of claim 1, additionally comprising a means for selectively venting the device.

4. The device of claim 1 wherein said top surface is slanted toward said dome to facilitate the collection of gas.

5. The device of claim 1 wherein opposite walls of said device are substantially mutually parallel.

6. The device of claim 1 wherein adjacent walls of said device are substantially mutually perpendicular.

7. The device of claim 1 wherein the base and the top surface of said device are constructed from transparent materials.

8. The device of claim 7 wherein said transparent material is plastic or glass.

9. A method for detecting the presence of a microorganism within a sample putatively containing a microorganism utilizing the device of claim 1, comprising the steps of:

adding growth medium to said device;

adding said sample to said growth medium, thereby forming a mixture;

incubating said mixture; and detecting the presence of said microorganism by determining the presence or absence of gas within said device.

10. The method of claim 9, additionally comprising, after the step of adding said sample, the steps of tilting said device such that the dome is filled with said mixture, and returning said device to an utilized position.

11. The method of claim 9 wherein said sample putatively containing a microorganism is a water sample.

12. The method of claim 9 wherein said sample putatively containing a microorganism is a food sample.

13. The method of claim 9 wherein said sample putatively containing a microorganism is a dairy sample.

14. The method of claim 9 wherein said sample putatively containing a microorganism is a biological fluid.

15. A method of analyzing a sample putatively containing a microorganism utilizing the device of claim 1, comprising the steps of:
adding growth medium containing a fluorogenic or chromogenic substrate to said device;
adding said sample to said growth medium, thereby forming a mixture;
incubating said mixture;
detecting the presence of said microorganism by determining the presence or absence of gas within said device; and
determining the presence of said microorganism by detecting the presence or absence of fluorescent or colored products within said growth medium.

16. The method of claim 15, additionally comprising, after the step of adding said sample, the steps of tilting said device such that the dome is filled with said mixture, and returning said device to an untilted position.

17. The method of claim 15 wherein said fluorogenic substrate is selected from the group consisting of fluorescein diacetate, 4-methylumbelliferyl acetate, 4-methylumbelliferyl-α-L-arabinopyranoside, 4-methylumbelliferyl casein, 4-methylumbelliferyl-β-D-fucopyranoside, 4-methylumbelliferyl-α-L-fucopyranoside, 4-methylumbelliferyl-β-L-fucopyranoside, 4-methylumbelliferyl-α-D-galactopyranoside, 4-methylumbelliferyl-β-D-galactopyranoside, 4-methylumbelliferyl-α-D-glucopyranoside, 4-methylumbelliferyl-β-D-glycopyranoside, 4-methylumbelliferyl-β-D-glucuronide, 4-methylumbelliferyl nonanoate, 4-methylumbelliferyl oleate, 4-methylumbelliferyl phosphate, bis(4-methylumbelliferyl)phosphate, 4-methylumbelliferyl pyrophosphate diester, and 4-methylumbelliferyl-β-D-xylopyranoside.

18. The method of claim 15 wherein said chromogenic substrate is selected from the group consisting of o-nitrophenyl-β-D-galactopyranoside, p-nitrophenyl-β-D-galactopyranoside, o-nitrophenyl-β-D-glucopyranoside, p-nitrophenyl-α-D-glucopyranoside, p-nitrophenyl-β-D-glucopyranoside, p-nitrophenyl-β-D-glucuronide, p-nitrophenyl phosphate, o-nitrophenyl-β-D-xylopyranoside, p-nitrophenyl-β-D-xylopyranoside, p-nitrophenyl-β-D-xylopyranoside, and phenolphthalein-β-D-glucuronide.

19. The method of claim 15 wherein said sample putatively containing a microorganism is a water sample.

20. The method of claim 15 wherein said sample putatively containing a microorganism is a food sample.

21. The method of claim 15 wherein said sample putatively containing a microorganism is a dairy sample.

22. The method of claim 15 wherein said sample putatively containing a microorganism is a biological fluid.

23. The method of claim 15 wherein said fluorescent product is detected by exposure to ultraviolet light.

24. An apparatus consisting of an array of adjacent, substantially identical devices, each device adapted for containing a volume of a growth medium and employed for detection of gas produced by a microorganism putatively contained within a test sample added to the growth medium of each device, each device comprising:
a primary chamber having a top surface and a base;
a dome defined by said top surface of said primary chamber and communicating therewith, said dome establishing a fluid level defined by the highest interior part of the dome, and being adapted for collection of gas produced within said grown medium;
a fill section adjacent to and communicating with one end of said primary chamber, said fill section spaced apart from said dome and extending above said fluid level, and further defining an opening for the addition of said test sample; and
a means for selectively closing said opening defined by said fill section.

25. The apparatus of claim 24 wherein said apparatus consists of a three-by-three array of said devices.

26. The apparatus of claim 24 wherein said apparatus consists of a three-by-five array of said devices.

27. The apparatus of claim 24 wherein said apparatus consists of a one-by-five array of said devices.

28. The apparatus of claim 24 wherein said apparatus consists of a five-by-five array of said devices.

29. The apparatus of claim 24 wherein said closure means covers the fill section of each of said devices.

30. The apparatus of claim 24, additionally comprising means for selectively venting each of said devices.

31. The apparatus of claim 24 wherein said apparatus is stackable on another of said devices.

32. The apparatus of claim 24 wherein said top surface is slanted toward the dome to facilitate the collection of said gas.

33. The apparatus of claim 24 wherein opposite walls of said devices are substantially mutually parallel.

34. The apparatus of claim 24 wherein adjacent walls of said devices are substantially mutually perpendicular.

35. The apparatus of claim 24 wherein the base and the top surface of said devices are constructed from transparent materials.

36. The apparatus of claim 35 wherein said transparent material is plastic or glass.

37. A method for detecting the presence of microorganisms in a plurality of samples, each putatively containing a microorganism, utilizing the apparatus of claim 24, comprising the steps of:
adding growth medium to at least two devices of said apparatus;
adding said samples to said devices containing said growth medium, thereby forming mixtures;
incubating said mixtures; and
detecting the presence of said microorganisms by determining the presence or absence of gas within each of said devices.

38. The method of claim 37, additionally comprising, after the step of adding said samples, the steps of tilting said apparatus such that the dome is filled with said mixtures, and returning said apparatus to an untilted position.

39. The method of claim 37 wherein said samples each putatively containing a microorganism are water samples.

40. The method of claim 37 wherein said samples each putatively containing a microorganism are food samples.

41. The method of claim 37 wherein said samples each putatively containing a microorganism are dairy samples.

42. The method of claim 37 wherein said samples each putatively containing a microorganism are biological fluids.

43. A method for estimating the number of microorganisms within a sample utilizing the apparatus of claim 24, comprising the steps of:
adding growth medium to at least two devices of said apparatus;
adding serial dilutions of a sample containing at least one microorganism to said devices containing said growth medium, thereby forming mixtures;
incubating said mixtures;
detecting the presence of said microorganisms by determining the presence or absence of gas within each device; and
estimating the number of said microorganisms within said sample.

44. The method of claim 43, additionally comprising, after the step of adding said serial dilutions, the steps of tilting said apparatus such that the dome is filled with said mixtures, are returning said apparatus to an untilted position.

45. The method of claim 43 wherein said sample containing a microorganism is a water sample.

46. The method of claim 43 wherein said sample containing a microorganism is a food sample.

47. The method of claim 43 wherein said sample containing a microorganism is a dairy sample.

48. The method of claim 43 wherein said sample containing a microorganism is a biological fluid.

49. The method of claim 43 wherein the number of said microorganisms is determined by the most-probable number procedure.

50. A method for analyzing a plurality of samples, each putatively containing a microorganism, utilizing the apparatus of claim 24, comprising the steps of:
adding growth medium containing a fluorogenic or chromogenic substrate to at least two devices of said apparatus;
adding said samples to said devices containing said growth medium, thereby forming mixtures;
incubating said mixtures;
detecting the presence of said microorganism by determining the presence or absence of gas within each device; and
determining the presence of said microorganism by detecting the presence or absence of fluorescent or colored products within said growth medium.

51. The method of claim 50, additionally comprising, after the step of adding said samples, the steps of tilting said apparatus such that the dome is filled with said mixtures, and returning said apparatus to an untilted position.

52. The method of claim 50 wherein said fluorogenic substrate is selected from the group consisting of fluorescein diacetate, 4-methylumbelliferyl acetate, 4-methylumbelliferyl-α-L-arabinopyranoside, 4-methylumbelliferyl casein, 4-methylumbelliferyl-β-D-fucopyranoside, 4-methylumbelliferyl-α-L-fucopyranoside, 4-methylumbelliferyl-β-L-fucopyranoside, 4-methylumbelliferyl-α-D-galactopyranoside, 4-methylumbelliferyl-β-D-galactopyranoside, 4-methylumbelliferyl-α-D-glucopyranoside, 4-methylumbelliferyl-β-D-glycopyranoside, 4-methylumbelliferyl-β-D-glucuronide, 4-methylumbelliferyl nonanoate, 4-methylumbelliferyl oleate, 4-methylumbelliferyl phosphate, bis(4-methylumbelliferyl)phosphate, 4-methylumbelliferyl pyrophosphate diester, and 4-methylumbelliferyl-β-D-xylopyranoside.

53. The method of claim 50 wherein said chromogenic substrate is selected from the group consisting of o-nitrophenyl-β-D-galactopyranoside, p-nitrophenyl-β-D-galactopyranoside, o-nitrophenyl-β-D-glucopyranoside, p-nitrophenyl-α-D-glucopyranoside, p-nitrophenyl-β-D-glucopyranoside, p-nitrophenyl-β-D-glucuronide, p-nitrophenyl phosphate, o-nitrophenyl-β-D-xylopyranoside, p-nitrophenyl-α-D-xylopyranoside, p-nitrophenyl-β-D-xylopyranoside, and phenolphthalein-β-D-glucuronide.

54. The method of claim 50 wherein said samples each putatively containing a microorganism are water samples.

55. The method of claim 50 wherein said samples each putatively containing a microorganism are food samples.

56. The method of claim 50 wherein said samples each putatively containing a microorganism are dairy samples.

57. The method of claim 50 wherein said samples each putatively containing a microorganism are biological fluids.

58. The method of claim 50 wherein said fluorescent product is detected by exposure to ultraviolet light.

59. A method of analyzing microorganisms within a sample utilizing the apparatus of claim 24, comprising the steps of:
adding growth medium containing a fluorogenic or chromogenic substrate to at least two devices of said apparatus;
adding serial dilutions of a sample containing at least one microorganism to said devices containing said growth medium, thereby forming mixtures;
incubating said mixtures;
detecting the presence of said microorganisms by determining the presence or absence of gas within each device;
determining the presence of said microorganisms by detecting the presence or absence of fluorescent or colored products within said growth medium; and
estimating the number of microorganisms within said sample.

60. The method of claim 59, additionally comprising, after the step of adding said serial dilutions, the steps of tilting said apparatus such that the dome is filled with said mixtures, and returning said apparatus to an untilted position.

61. The method of claim 59 wherein said fluorogenic substrate is selected from the group consisting of fluorescein diacetate, 4-methylumbelliferyl acetate, 4-methylumbelliferyl-α-L-arabinopyranoside, 4-methylumbelliferyl casein, 4-methylumbelliferyl-β-D-fucopyranoside, 4-methylumbelliferyl-α-L-fucopyranoside, 4-methylumbelliferyl-β-L-fucopyranoside, 4-methylumbelliferyl-α-D-galactopyranoside, 4-methylumbelliferyl-β-D-galactopyranoside, 4-methylumbelliferyl-α-D-glucopyranoside, 4-methylumbelliferyl-β-D-glycopyranoside, 4-methylumbelliferyl-β-D-glucuronide, 4-methylumbelliferyl nonanoate, 4-methylumbelliferyl oleate, 4-methylumbelliferyl phosphate, bis(4-methylumbelliferyl)phosphate, 4-methylumbelliferyl pyrophosphate diester, and 4-methylumbelliferyl-β-D-xylopyranoside.

62. The method of claim 59 wherein said chromogenic substrate is selected from the group consisting of o-nitrophenyl-$\beta$-D-galactopyranoside, p-nitrophenyl-$\beta$-D-galactopyranoside, o-nitrophenyl-$\beta$-D-glucopyranoside, p-nitrophenyl-$\alpha$-D-glucopyranoside, p-nitrophenyl-$\beta$-D-glucopyranoside, p-nitrophenyl-$\beta$-D-glucuronide, p-nitrophenyl phosphate, o-nitrophenyl-$\beta$-D-xylopyranoside, p-nitrophenyl-$\alpha$-D-xylopyranoside, p-nitrophenyl-$\beta$-D-xylopyranoside, and phenolphthalein-$\beta$-D-glucuronide.

63. The method of claim 59 wherein said sample containing a microorganism is a water sample.

64. The method of claim 59 wherein said sample containing a microorganism is a food sample.

65. The method of claim 59 wherein said sample containing a microorganism is a dairy sample.

66. The method of claim 59 wherein said sample containing a microorganism is a biological fluid.

67. The method of claim 59 wherein the number of said microorganisms is determined by the most-probable number procedure.

68. The method of claim 59 wherein said fluorescent end product is detected by exposure to ultraviolet light.

* * * * *

UNITED STATES PATENT AND TRADEMARK OFFICE
CERTIFICATE OF CORRECTION

PATENT NO. : 4,868,110

DATED : September 19, 1989

INVENTOR(S) : John P. DesRosier; Robert Ward, Jr.

It is certified that error appears in the above-identified patent and that said Letters Patent is hereby corrected as shown below:

In claim 10, column 14, line 68, delete "utilized" and substitute therefor --untilted--.

In claim 44, column 17, line 24, delete "are" and substitute therefor --and--.

Signed and Sealed this

Eighteenth Day of September, 1990

*Attest:*

HARRY F. MANBECK, JR.

*Attesting Officer*      *Commissioner of Patents and Trademarks*